United States Patent
Kaminski et al.

(10) Patent No.: US 9,913,819 B2
(45) Date of Patent: Mar. 13, 2018

(54) METHODS OF TREATING OR PREVENTING FIBROTIC LUNG DISEASES

(71) Applicant: YALE UNIVERSITY, New Haven, CT (US)

(72) Inventors: Naftali Kaminski, New Haven, CT (US); Argyrios Tzouvelekis, New Haven, CT (US); Guoying Yu, New Haven, CT (US)

(73) Assignee: Yale University, New Haven, CT (US)

(*) Notice: Subject to any disclaimer, the term of this patent is extended or adjusted under 35 U.S.C. 154(b) by 0 days.

(21) Appl. No.: 15/317,276

(22) PCT Filed: Jun. 11, 2015

(86) PCT No.: PCT/US2015/035308
§ 371 (c)(1),
(2) Date: Dec. 8, 2016

(87) PCT Pub. No.: WO2015/191841
PCT Pub. Date: Dec. 17, 2015

(65) Prior Publication Data
US 2017/0105956 A1    Apr. 20, 2017

Related U.S. Application Data

(60) Provisional application No. 62/011,195, filed on Jun. 12, 2014.

(51) Int. Cl.
*A61K 31/198* (2006.01)
*A61K 9/00* (2006.01)
*A61K 45/06* (2006.01)

(52) U.S. Cl.
CPC .......... *A61K 31/198* (2013.01); *A61K 9/0075* (2013.01); *A61K 45/06* (2013.01)

(58) Field of Classification Search
CPC ..... A61K 31/198; A61K 45/06; A61K 9/0075
See application file for complete search history.

(56) References Cited

U.S. PATENT DOCUMENTS

2005/0232923 A1    10/2005    Yan et al.

FOREIGN PATENT DOCUMENTS

WO    2013148232 A1    10/2013

OTHER PUBLICATIONS

DIO2 from Wikipedia, 2017.*
International Search Report and Written Opinion for PCT International Application No. PCT/US2015/035308 dated Sep. 30, 2015.
"Role of DIO2 in Idiopathic Pulmonary Fibrosis", American Thoracic Society International Conference, Poster, Abstract, May 18, 2012.
"Up-regulation of DIO2 in Idiopathic Pulmonary Fibrosis", American Thoracic Society International Conference, Poster, May 18, 2012.

* cited by examiner

*Primary Examiner* — Sudhakar Katakam
(74) *Attorney, Agent, or Firm* — Saul Ewing Arnstein & Lehr LLP; Kathryn Doyle; Domingos J. Silva

(57) ABSTRACT

The invention includes a method of preventing or treating a fibrotic lung disease in a subject, comprising administering to the subject a thyroid hormone by inhalation and/or aerosolization. The invention further comprises compositions and kits comprising compositions useful within the invention.

15 Claims, 15 Drawing Sheets

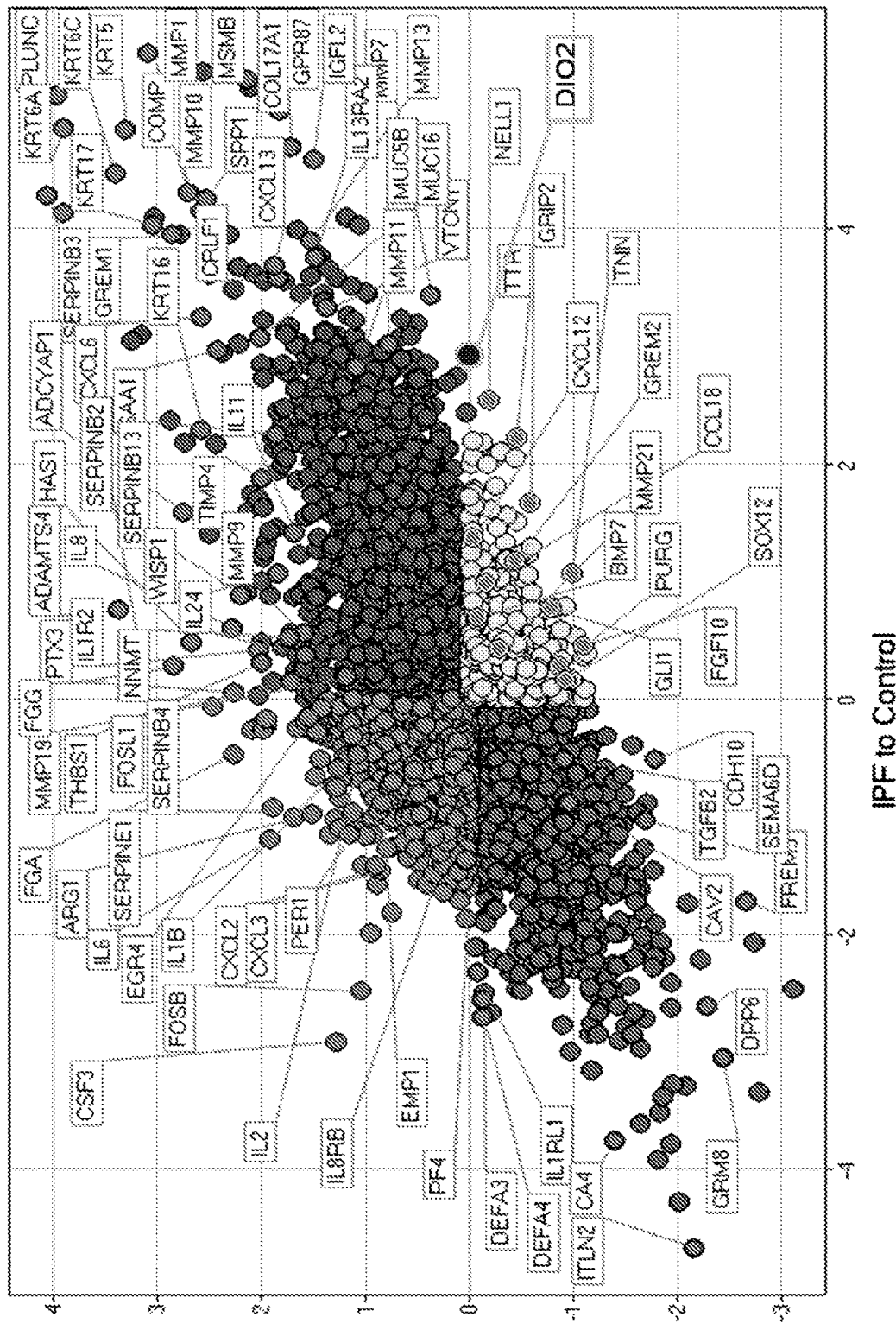

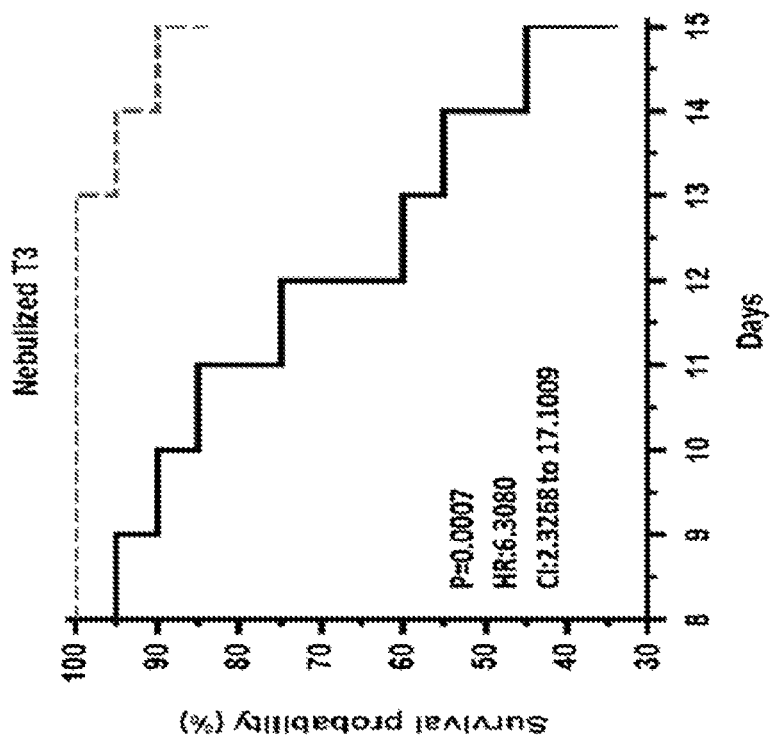
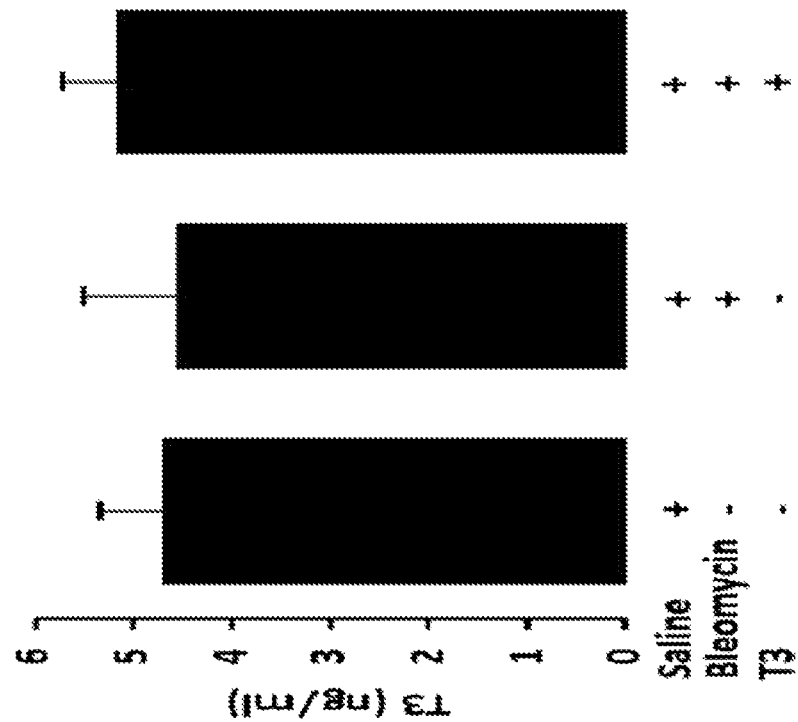
FIG. 5E
FIG. 5F

METHODS OF TREATING OR PREVENTING FIBROTIC LUNG DISEASES

CROSS-REFERENCE TO RELATED APPLICATIONS

The present application is a 35 U.S.C. § 371 national phase application from, and claims priority to, International Application No. PCT/US2015/035308, filed Jun. 11, 2015, and published under PCT Article 21(2) in English, which claims priority to U.S. Provisional Application No. 62/011,195, filed Jun. 12, 2014, all of which applications are incorporated herein by reference in their entireties.

BACKGROUND OF THE INVENTION

Idiopathic pulmonary fibrosis (IPF) is a devastating chronic lung disease with yet unknown etiology. IPF leads to death in 3.5-4 years from initial diagnosis in more than 50% of the patients, irrespective of treatment (Travis, et al., 2013, Am. J. Resp. Crit. Care Med. 188:733-748). Despite extensive research efforts, its pathogenesis is still elusive and controversial (Selman, et al., 2001, Ann. Int. Med. 134:136-151; Selman, et al., 2008, PLoS Med. 5:e62). See also www dot ncbi dot nlm dot nih dot gov/pubmed/24875841; www dot nejm dot org/doi/full/10 dot 1056/NEJMoa1402584; www dot nejm dot org/doi/full/10 dot 1056/NEJMoa1402582.

With a gradually increasing worldwide incidence and no proven therapies other than lung transplantations, IPF treatment represents a major challenge for both pharmaceutical industries and chest physicians. To date, all available treatment agents have been delivered systemically, either orally or subcutaneously. In addition to their limited therapeutic efficacy, use of the majority of these agents has been associated with side effects, ranging from major side effects (such as immune suppression and subsequent infections, acute exacerbations of disease and excessive bleeding) to minor side effects (including gastrointestinal complications, such as diarrhea and nausea) that significantly affect patient quality of life. So far, none of the agents tried, had any significant effect on patient survival.

Early during embryonic development, definitive embryonic progenitor cells of the developing foregut become committed to various organ domains including the lung and thyroid. In line with the premise of common embryonic origin, lung and thyroid share several common transcriptional regulators of their development such as Nkx2-1 and thyroid transcription factor (TTF)-1. In particular, Nkx2-1 knockout mice display lung and thyroid agenesis, while humans born with Nkx2-1 gene mutations develop pediatric lung disease, hypothyroidism and neurological impairment. In addition, TTF-1, a 38KD nuclear transcription factor that belongs in the Nkx2 superfamily and is predominantly found in both normal type II alveolar epithelial cells and thyroid tissue, plays an essential role in epithelial morphogenesis, stimulating the synthesis of surfactant proteins and regulating secretory product gene transcription in Clara cells. TTF-1 is used by pathologists as a reliable histologic marker in the differential diagnosis of both thyroid tumors as well as pulmonary adenocarcinoma. Studies in murine models have shown that exogenous administration of thyroid hormones (T4-thyroxine and its potent derivative-triiodothyronine-T3) accelerate surfactant production, alveolar formation and fetal lung maturation. Unfortunately, investigational trials of thyroid replacement therapy for premature infants with respiratory distress syndrome (RDS) showed mixed irreproducible results. The exact mechanisms through which thyroid hormones exert their therapeutic potentials are unknown, and these compounds have not been successfully used in the treatment of lung fibrosis.

There is a need in the art to identify novel therapeutic treatments that can be used to treat or prevent fibrotic lung diseases, such as idiopathic pulmonary fibrosis. The present invention addresses and meets this need.

BRIEF SUMMARY OF THE INVENTION

The invention includes a method of preventing or treating a fibrotic lung disease in a subject in need thereof. The invention further includes a method of identifying therapeutic treatment for a subject afflicted with a fibrotic lung disease. The invention further includes a kit comprising at least one thyroid hormone, an applicator, and an instructional material for use thereof.

In certain embodiments, the method comprises administering to the subject a therapeutically effective amount of at least one thyroid derivative using an administration route selected from the group consisting of nasal, inhalational, intratracheal, intrapulmonary, intrabronchial, and inhalation.

In certain embodiments, the method comprises assaying lung tissue of the subject for DIO2 levels, wherein, if DIO2 levels in the lung tissue of the subject are upregulated with respect to a subject not afflicted with the disease, the subject is administered a therapeutically effective amount of T4 hormone using an administration route selected from the group consisting of nasal, inhalational, intratracheal, intrapulmonary, intrabronchial, and inhalation.

In certain embodiments, the thyroid derivative comprises a thyroid hormone. In other embodiments, the hormone comprises T3 hormone or T4 hormone. In yet other embodiments, the hormone is T3 hormone or T4 hormone. In yet other embodiments, the thyroid derivative comprises T4 hormone.

In certain embodiments, the lung tissue of the subject has upregulated DIO2 levels as compared to a subject who is not afflicted with the disease, and wherein the thyroid hormone comprises T4 hormone. In other embodiments, the lung tissue of the subject has DIO2 levels that are at least about 50% higher than those in a subject not afflicted by the disease. In yet other embodiments, the lung tissue of the subject has DIO2 levels that are at least about 100% higher than those in a subject not afflicted by the disease. In yet other embodiments, the DIO2 levels are upregulated in terms of at least one selected from the group consisting of gene expression, mRNA expression and protein expression. In yet other embodiments, the fibrotic lung disease comprises idiopathic pulmonary fibrosis. In yet other embodiments, the lung tissue of the subject has upregulated DIO2 levels as compared to a subject who is not afflicted with the disease, and wherein the thyroid hormone comprises T4 hormone.

In certain embodiments, the subject is further administered at least one additional agent that treats, prevents or reduces the symptoms of the fibrotic lung disease. In other embodiments, the kit further comprises at least one additional agent that treats, prevents or reduces the symptoms of the fibrotic lung disease. In yet other embodiments, the at least one additional agent comprises pirfenidone or nintadanib. In yet other embodiments, the thyroid derivative is administered to the subject at a frequency selected from the group consisting of about three times a day, about twice a day, about once a day, about every other day, about every third day, about every fourth day, about every fifth day, about every sixth day and about once a week. In yet other embodiments, the thyroid derivative is formulated as a dry powder blend. In yet other embodiments, the dry powder blend comprising levothyroxine sodium hydrate. In yet other embodiments, the dry powder blend further comprises lactose particles, comprising lactose.$H_2O$, gelatine and starch maize; sodium starch glycolate; magnesium stearate; and talc silicified, comprising talc purified and colloidal silicon dioxide. In yet other embodiments, the subject is a mammal. In yet other embodiments, the mammal is a human.

In certain embodiments, the DIO2 levels are upregulated in terms of at least one selected from the group consisting of gene expression, mRNA expression and protein expression.

In certain embodiments, the instructional material comprises instructions for preventing or treating a fibrotic lung disease in a subject using an administration route selected from the group consisting of nasal, inhalational, intratracheal, intrapulmonary, intrabronchial, and inhalation, wherein the thyroid hormone comprises T3 hormone or T4 hormone. In other embodiments, the instructional material comprises instructions that a subject with upregulated DIO2 levels in the lung tissue, as compared to a subject not afflicted with the disease, is to be administered a therapeutically effective amount of T4 hormone. In yet other embodiments, the thyroid derivative is formulated as a dry powder blend. In yet other embodiments, the dry powder blend comprises levothyroxine sodium hydrate. In yet other embodiments, the dry powder blend further comprises lactose particles, comprising lactose.$H_2O$, gelatine and starch maize; sodium starch glycolate; magnesium stearate; and talc silicified, comprising talc purified and colloidal silicon dioxide.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIGS. 1A-1K illustrate the finding that DIO2 is highly upregulated in IPF lungs. FIG. 1A: Gene expression analysis using microarray platforms demonstrates DIO2 as one of the most upregulated genes (p=5.4E-7, fold change 8.49) that clearly differentiated patients with IPF (n=89) from controls (n=43), and emphysema subjects. FIG. 1B: DIO2 mRNA expression was detected by qRT-PCR in the lungs of IPF patients (n=53) and control subjects (n=17). FIG. 1C: DIO2 protein expressions as detected by immunoblot analysis in lung tissue samples from IPF patients (n=6) and control subjects (n=3). FIG. 1D: Densitometry analysis of the immunoblot as image C. FIGS. 1E-1J: Immunohistochemical analysis of DIO2 expression in lung tissue sections; FIG. 1E: Representative image from normal lungs; FIGS. 1F-1J: Representative images from IPF lungs; FIG. 1K: DIO2 enzymatic activities in IPF lungs compared with normal lung tissues and lung tumors.

FIG. 2A: Hydroxyproline content was measured in the right lungs of wild-type (WT) and DIO2 KO mice at day 7 and day 14 (n=8 in each group). FIG. 2B: Col1a1 mRNA expression was detected by qRT-PCR in the lungs of WT and DIO2 KO mice (n=8 in each group). FIG. 2C: Col3a1 mRNA expression was detected by qRT-PCR in the lungs of WT and DIO2 KO mice (n=8 in each group). FIG. 2D: Masson trichrome staining of lungs of WT and DIO2 KO mice. FIG. 2E: Immunohistochemical analysis of alpha smooth muscle actin expression in lung tissue sections of WT and DIO2 KO mice (day 14).

FIG. 3A: Hydroxyproline content was measured in the right lungs of treated and control mice at day 14 (n=8 in each group). FIG. 3B: Collagen content was measured in the right lungs of the treated and control mice at day 14 (n=8 in each group). FIG. 3C: Col1a1 and Col3a1 mRNA expression were detected by qRT-PCR in the lungs of the treated and control mice (n=8 in each group).

FIG. 4A: Hydroxyproline measurements showed a significant increase following bleomycin treatment in both saline and PTU treatment groups, while there was no statistical difference in the T4 treated group from the saline group when T4 was injected at day 3. FIG. 4B: QRT-PCR analysis indicates that T4 treatment markedly suppresses targeted gene expressions of Col1a1, Col3a1, S100a4 and Acta2 (n=8, p<0.05) when T4 was injected at day 3. FIG. 4C: Hydroxyproline measurements showed a significant increase following bleomycin treatment in both saline and PTU treatment groups, while there was no statistical difference in the T4 treated group from the saline group when T4 was injected at day 7. FIG. 4D: QRT-PCR analysis indicates that T4 treatment significantly suppresses targeted gene expressions of Col1a1, Col3a1, S100a4 and Acta2 (n=8, p<0.05) when T4 was injected at day 7 as well. FIG. 4E: T4 systematic administration resulted into a statistically significant increase in circulating levels of T3 (n=10, p<0.05). FIG. 4F: Relative relationship between T3 level in the serum and hydroxyproline content in the mouse lungs. FIG. 4G: Histological examination by masson trichrome staining showed that the fibrotic and inflammatory response to bleomycin were attenuated by T4 treatment at either day 3 or day 7.

FIGS. 5A-5F illustrate the finding that T3 inhalation blunts bleomycin-induced fibrosis and reduces mortality. 40 μg/kg of T3 was nebulized and inhaled day 10, 12, 14, 16 after bleomycin treatment at dose of 1.5 U/kg, Saline as control. Mice were sacrificed at day 21. FIG. 5A: Hydroxyproline measurements showed a significant increase following bleomycin treatment and T3 inhalation at dose of 40 μg/kg declines hydroxyproline content. FIG. 5B: Col1a1 mRNA expression was detected by QRT-PCR (n=8 in each group). FIG. 5C: Col3a1 mRNA expression was detected by QRT-PCR. FIG. 5D: T3 level in the sera by ELISA showing T3 inhalation does not affect the level of T3 (n=10, p<0.05) in sera of treated mice. FIG. 5E: TSH level in the sera showed that T3 inhalation does not significantly increase the TSH concentration in the sera of the mice (n=10, p<0.05). FIG. 5F: Bleomycin-induced mortality by Kaplan-Meier survival curve analysis. 4.5 U/kg of bleomycin was delivered intratracheally at day 0, 40 µg/kg of T3 was nebulized and inhaled every other day since day 7, saline treatment as control group.

DETAILED DESCRIPTION OF THE INVENTION

Figure 1D:
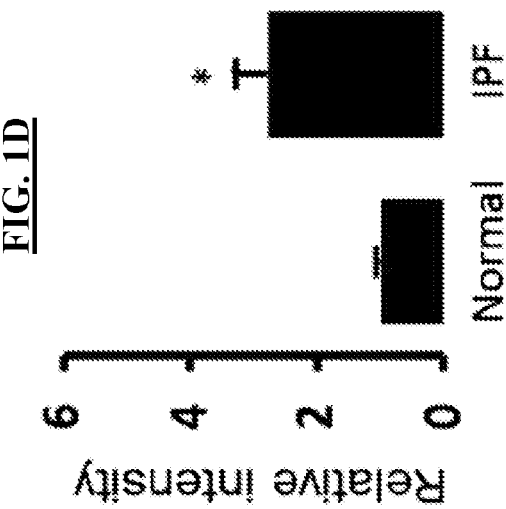
Figure 1B:
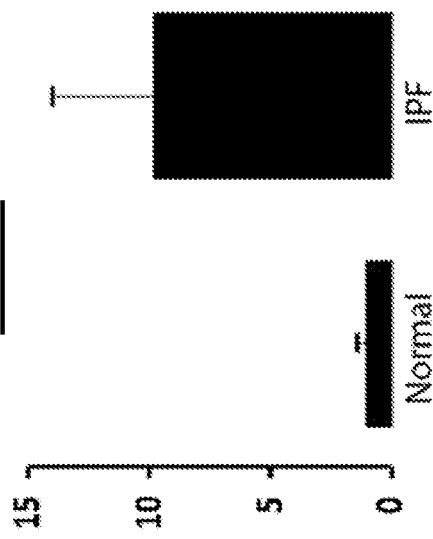
Figure 1C:
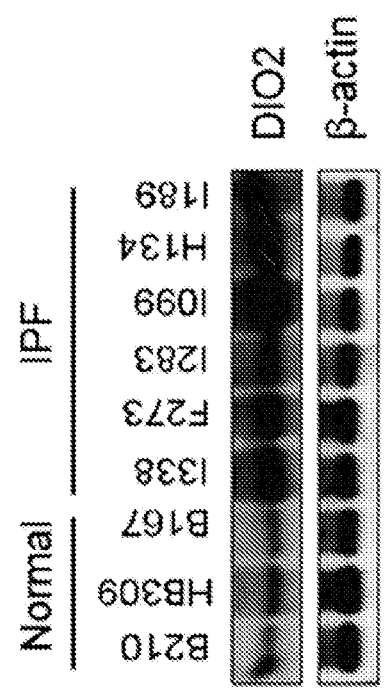
Figure 1G:
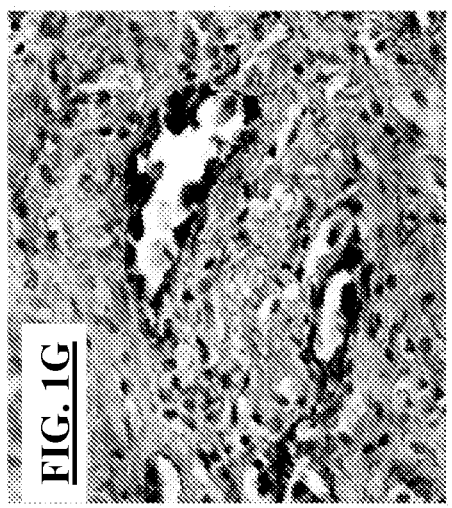
Figure 1J:
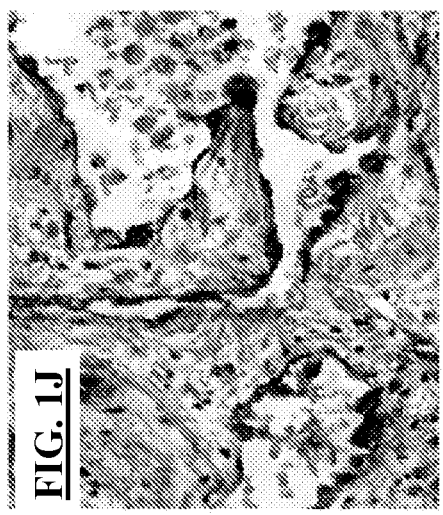
Figure 1F:
Figure 1I:
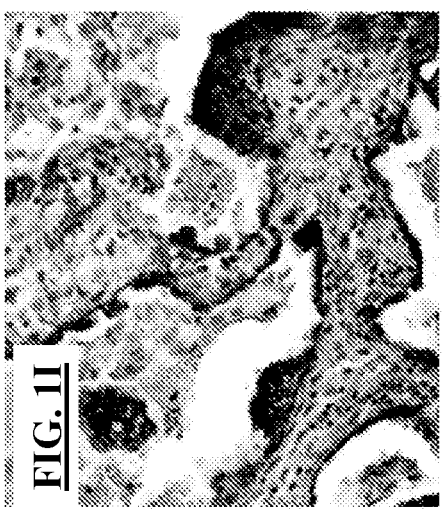

The present invention relates in part to the unexpected discovery that targeted administration of a thyroid derivative to a subject afflicted with a fibrotic lung disease results in attenuation or complete resolution of the fibrotic process in the subject. In certain embodiments, the thyroid derivative comprises a thyroid hormone. In other embodiments, the thyroid hormone comprises T3 hormone and/or T4 hormone. In yet other embodiments, the thyroid hormone is aerosolized. In yet other embodiments, the lung tissue in the subject has upregulated DIO2 levels, wherein DIO2 is an enzyme that catalyzes the conversion of T4 to its active component T3. In yet other embodiments, the subject which lung tissue has upregulated DIO2 levels is administered T4 hormone.

The studies reported herein indicate that inhibition of thyroid hormone enhances lung fibrosis, and local administration of aerosolized thyroid hormone blunts pulmonary fibrosis in animal models of lung fibrosis. These results support the therapeutic potential of aerosolized administration of thyroid hormone to subjects suffering from fibrotic lung diseases. In certain embodiments, targeted administration of thyroid derivatives within injured lung attenuate or completely resolve the fibrotic process.

In certain embodiments, the thyroid hormone T3 is directly delivered into the lung using an inhaler. In other embodiments, the thyroid hormone T4 is directly delivered into the lung using an inhaler. This allows for effective delivery of an optimal drug dose within areas of injured lung, maximizing its therapeutic effects and minimizing potential side effects arising from systemic administration.

As reported herein, animal studies include the delivery of T4 to mouse injured lung following bleomycin exposure via repeated inhalations during various time points of the disease course. In the preventive approach; T4 is inhaled at day 0 following bleomycin exposure. In the therapeutic approach, T4 is repeatedly inhaled (every day) at days 7-14 (inflammatory stage) and at days 14-21 (fibrotic stage) following bleomycin exposure.

In certain embodiments, IPF subjects with upregulated DIO2 expression are administered T4 hormone to treat or prevent the fibroid process. Without wishing to be limited by any theory, this allows for the identification of those patients that will most likely benefit from the treatment with a thyroid hormone. In other embodiments, the invention provides a method of selecting those subjects afflicted with IPF that will most likely benefit from the treatment with a thyroid hormone.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, non-limiting methods and materials are described.

As used herein, each of the following terms has the meaning associated with it in this section.

As used herein, the articles "a" and "an" are used o refer to one or to more than one (i.e., to at least one) of the grammatical object of the article. By way of example, "an element" means one element or more than one element.

As used herein, "about," when referring to a measurable value such as an amount, a temporal duration, and the like, is meant to encompass variations of ±20% or ±10%, in certain embodiments ±5%, in certain embodiments ±1%, and in certain embodiments ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

In one aspect, the terms "co-administered" and "co-administration" as relating to a subject refer to administering to the subject a compound of the invention or salt thereof along with a compound that may also treat the disorders or diseases contemplated within the invention. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

As used herein, the term "DIO2" refers to the enzyme Type II iodothyronine deiodinase, iodothyronine 5'-deiodinase, or iodothyronine 5'-monodeiodinase. DIO2 activates thyroid hormone by converting the prohormone thyroxine (T4) by outer ring deiodination to bioactive 3,3',5-triiodothyronine (T3).

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "fibrotic lung disease" or "fibroid lung disease" or "pulmonary fibrosis" or "scarring of the lung" refers to a group of diseases characterized by the formation or development of excess fibrous connective tissue (fibrosis) in the lungs. Symptoms of pulmonary fibrosis are mainly: shortness of breath, particularly with exertion; chronic dry, hacking coughing; fatigue and weakness;

chest discomfort; and loss of appetite and rapid weight loss. Pulmonary fibrosis may be a secondary effect of other diseases, most of them being classified as interstitial lung diseases, such as autoimmune disorders, viral infections or other microscopic injuries to the lung. Pulmonary fibrosis can also appear without any known cause ("idiopathic"). Idiopathic pulmonary fibrosis is a diagnosis of exclusion of a characteristic set of histologic/pathologic features known as usual interstitial pneumonia (UIP).

Diseases and conditions that may cause pulmonary fibrosis as a secondary effect include: inhalation of environmental and occupational pollutants (asbestosis, silicosis and gas exposure); hypersensitivity pneumonitis, most often resulting from inhaling dust contaminated with bacterial, fungal, or animal products; cigarette smoking; connective tissue diseases such as rheumatoid arthritis, SLE; scleroderma, sarcoidosis and Wegener's granulomatosis; infections; medications such as amiodarone, bleomycin (pingyangmycin), busulfan, methotrexate, apomorphine and nitrofurantoin; and radiation therapy to the chest.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The terms "patient," "subject" or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions.

The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

As used herein, the term "T3" refers to (S)-triiodothyronine, liothyronine, (S)-2-amino-3-[4-(4-hydroxy-3-iodophenoxy)-3,5-diiodophenyl]propanoic acid, or a salt or solvate thereof.

As used herein, the term "T4" refers to (S)-thyroxine, (S)-2-amino-3-[4-(4-hydroxy-3,5-diiodophenoxy)-3,5-diiodophenyl]propanoic acid, or a salt or solvate thereof.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

By the term "specifically bind" or "specifically binds," as used herein, is meant that a first molecule preferentially binds to a second molecule (e.g., a particular receptor or enzyme), but does not necessarily bind only to that second molecule.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Compounds and Compositions

In certain embodiments, thyroid hormones are useful within the methods of the invention. Non-limiting examples of thyroid hormones contemplated within the invention include, but are not limited to, T4 hormone, or a salt or solvate thereof.

Compositions comprising a thyroid hormone are also contemplated within the invention.

Methods

The invention includes a method of preventing or treating a fibrotic lung disease in a subject in need thereof. In certain embodiments, the method comprises administering to the subject therapeutically effective amounts of at least one thyroid derivative. In other embodiments, the route of administration is selected from the group consisting of nasal, inhalational, intratracheal, intrapulmonary, intrabronchial, and inhalation.

In certain embodiments, the thyroid derivative comprises a thyroid hormone. In other embodiments, the hormone comprises T3 hormone and/or T4 hormone. In yet other embodiments, the thyroid hormone is T3 hormone and/or T4 hormone.

In certain embodiments, the lung tissue of the subject has upregulated DIO2 levels as compared to a subject who is not afflicted with the disease. In other embodiments, the lung tissue of the subject has DIO2 levels that are at least about 50% higher, or at least about 75% higher, or at least about 100% higher, or at least about 125% higher, or at least about 150% higher, or at least about 175% higher, or at least about 200% higher, or at least about 225% higher, or at least about 250% higher, or at least about 275% higher, or at least about 300% higher, or at least about 350% higher, or at least about 400% higher, or at least about 500% higher, or at least about 550% higher, or at least about 600% higher, or at least about 650% higher, or at least about 700% higher, or at least about 750% higher, or at least about 800% higher, or at least about 900% higher, or at least about 1,000% higher, or higher than about 1,000% than those in a subject not afflicted by the disease. In yet other embodiments, the upregulated DIO2 levels are measured in terms of gene expression, mRNA expression and/or protein expression.

In certain embodiments, the fibrotic lung disease comprises idiopathic pulmonary fibrosis.

In certain embodiments, the compositions of the invention are administered to the subject about three times a day, about twice a day, about once a day, about every other day, about every third day, about every fourth day, about every fifth day, about every sixth day and/or about once a week.

In certain embodiments, the subject is further administered at least one additional bioactive agent that treats, prevents or reduces the symptoms of the fibrotic lung disease.

In certain embodiments, the subject is a mammal. In other embodiments, the mammal is a human.

In certain embodiments, the composition is administered to the subject by at least one route selected from the group consisting of nasal, inhalational, intratracheal, intrapulmonary, intrabronchial, and inhalation.

Kits

The invention includes a kit comprising at least a thyroid hormone, an applicator, and an instructional material for use thereof. The instructional material included in the kit comprises instructions for preventing or treating a fibrotic lung disease contemplated within the invention in a subject. The instructional material recites the amount of, and frequency with which, the at least one thyroid hormone should be administered to the subject. In other embodiments, the kit further comprises at least one additional bioactive agent that treats, prevents or reduces the symptoms of a fibrotic lung disease.

Combination Therapies

In certain embodiments, the compounds of the invention are useful in the methods of the invention in combination with at least one additional compound useful for treating or preventing fibrotic lung disease. This additional compound may comprise compounds identified herein or compounds, e.g., commercially available compounds, known to treat, prevent or reduce the symptoms of fibrotic lung disease.

Non-limiting examples of additional compounds contemplated within the invention include pirfenidone (5-methyl-1-phenylpyridin-2-one, or a salt or solvate thereof) and nintadanib (methyl (3Z)-3-{[(4-{methyl[(4-methylpiperazin-1-yl)acetyl]amino}phenyl)amino] (phenyl)methylidene}-2-oxo-2,3-dihydro-1H-indole-6-carboxylate, or a salt or solvate thereof).

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, such as a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The therapeutically effective amount or dose of a compound of the present invention depends on the age, sex and weight of the patient, the current medical condition of the patient and the progression of a disease or disorder contemplated in the invention.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies in certain embodiments within a range of circulating concentrations that include the $ED_{50}$ with minimal toxicity. The dosage optionally varies within this range depending upon the dosage form employed and the route of administration utilized.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal and the like. In many cases, it is advisable to include isotonic agents, for example, sugars, sodium chloride, or polyalcohols such as mannitol and sorbitol, in the composition.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for any suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., analgesic agents.

Routes of administration of any of the compositions of the invention include nasal, inhalational, intratracheal, intrapulmonary, intrabronchial, and inhalation.

Suitable compositions and dosage forms include, for example, dispersions, suspensions, solutions, syrups, granules, beads, powders, pellets, liquid sprays for nasal or oral administration, dry powder or aerosolized formulations for inhalation, and the like. It should be understood that the formulations and compositions that would be useful in the present invention are not limited to the particular formulations and compositions that are described herein.

Powdered and granular formulations of a pharmaceutical preparation of the invention may be prepared using known methods. Such formulations may be administered directly to a subject, used, for example, to form a material that is suitable to administration to a subject. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may be prepared, packaged, or sold in a formulation suitable for pulmonary administration via the buccal cavity. Such a formulation may comprise dry particles that comprise the active ingredient and have a diameter in the range from about 0.5 to about 7 nanometers, and in certain embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In certain embodiments, such powders comprise particles wherein at least 98% of the particles by weight have a diameter greater than 0.5 nanometers and at least 95% of the particles by number have a diameter less than 7 nanometers. In certain embodiments, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in certain embodiments having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration in certain embodiments have an average diameter in the range from about 0.1 to about 200 nanometers.

The pharmaceutical composition of the invention may be delivered using an inhalator such as those recited in U.S. Pat. No. 8,333,192 B2, which is incorporated herein by reference in its entirety.

In certain embodiments, the composition of the invention comprises a stable dry powder blend containing levothyroxine sodium hydrate; lactose particles, comprising lactose $H_2O$, gelatin and starch maize; sodium starch glycolate; magnesium stearate; and talc silicified, comprising talc purified and colloidal silicon dioxide. In other embodiments, the dry powder comprises levothyroxine sodium is in an amount 4 to 0.02 mg per 100 mg of the dry powder. In yet other embodiments, the dry powder comprises lactose in an amount higher than 90 mg per 100 mg of the dry powder preparation. In yet other embodiments, the dry powder comprises lactose particles consisting of lactose $H_2O$, gelatin and starch maize, wherein the ratio by weight-mg of: "lactose $H_2O$":"gelatin":"starch maize" is 55-75:0.20-0.80: 20-40. In yet other embodiments, the dry powder comprises sodium starch glycolate in an amount of 4-8 mg per 100 mg of dry powder. In yet other embodiments, the dry powder comprises magnesium stearate in an amount of 0.5-2 mg per 100 mg of dry powder. In yet other embodiments, the dry powder comprises talc silicified, in an amount of 2 mg per 100 mg of dry powder, wherein the talc silicified comprises talc purified and colloidal silicon dioxide in an amount of 0.667 mg of talc purified and 1.333 mg of colloidal silicon dioxide for 2 mg of talc silicified. In yet other embodiments, the blend further comprises a lake. In yet other embodiments, the dry powder comprises sodium starch glycolate in an amount of 5-6 mg per 100 mg of dry powder. In yet other embodiments, the dry powder comprises magnesium stearate in an amount of 1 mg per 100 mg of dry powder.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1: Gene Expression Analysis and Validation Experiments

DIO2 is an enzyme that catalyzes the conversion of the pro-hormone T4 into its potent derivative T3, which binds with high affinity with the nuclear thyroid hormone receptor and influences the expression of an entire gene network involved in cellular metabolism and stress response.

High-throughput gene expression analysis using microarray platforms in 303 tissue samples from patients with IPF derived from LTRC indicated that type II iodothyronine deiodinase (DIO2) is one of the most upregulated genes that clearly differentiated patients with IPF from controls and subjects with emphysema (FIGS. 1A-1K).

Figure 1E:
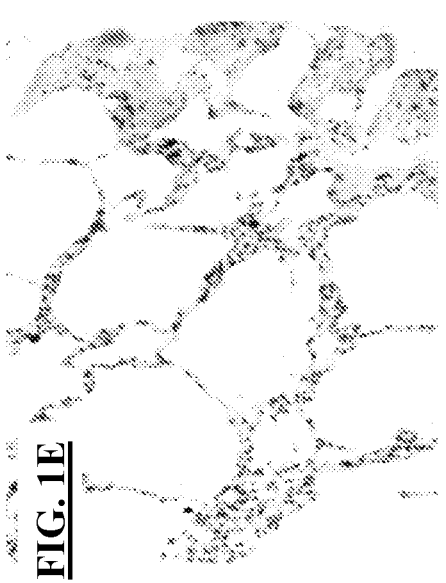
Figure 1H:
Figure 1K:
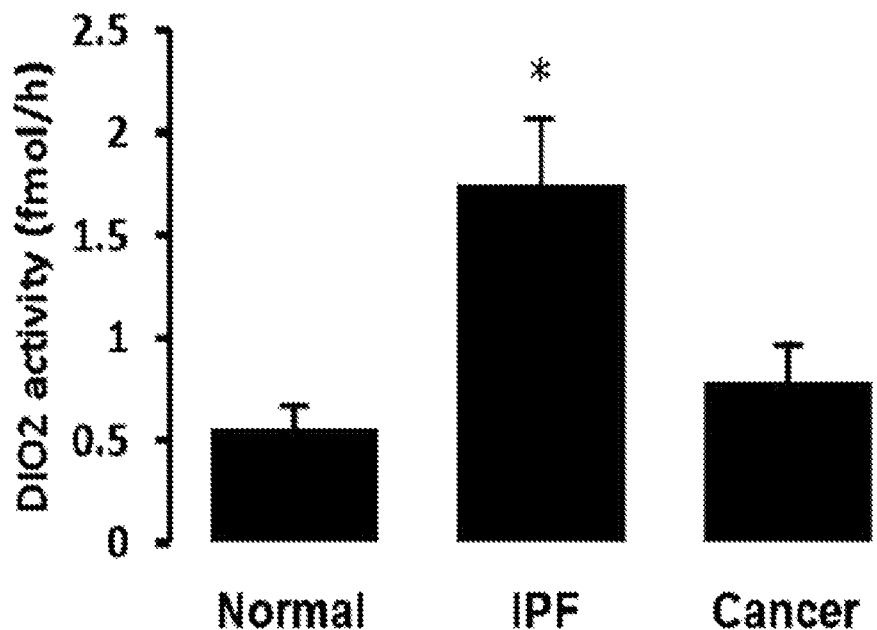

Gene expression data (FIGS. 1A-1B) were further validated on a protein level as indicated by immunoblot (FIG. 1C) and immunohistochemistry analysis, showing increased staining intensity within the alveolar epithelium surrounding areas of fibroblastic foci (FIGS. 1F-1J) compared to control lung specimens (FIG. 1E). In addition, DIO2 enzymatic activity was upregulated in IPF tissue extracts compared to control specimens, as assessed by the calculation of T4 to T3 conversion on the rate of $^{125}$I-release using a specific luciferase activity kit (FIG. 1K).

Example 2: Experimental Model of Lung Fibrosis in DIO2 Knockout Mice

To further implicate DIO2 mRNA and protein upregulation in the pathogenetic cascade of lung fibrosis, DIO2 knockout were treated with bleomycin, which is an agent commonly used to cause lung fibrosis.

Figure 2A:
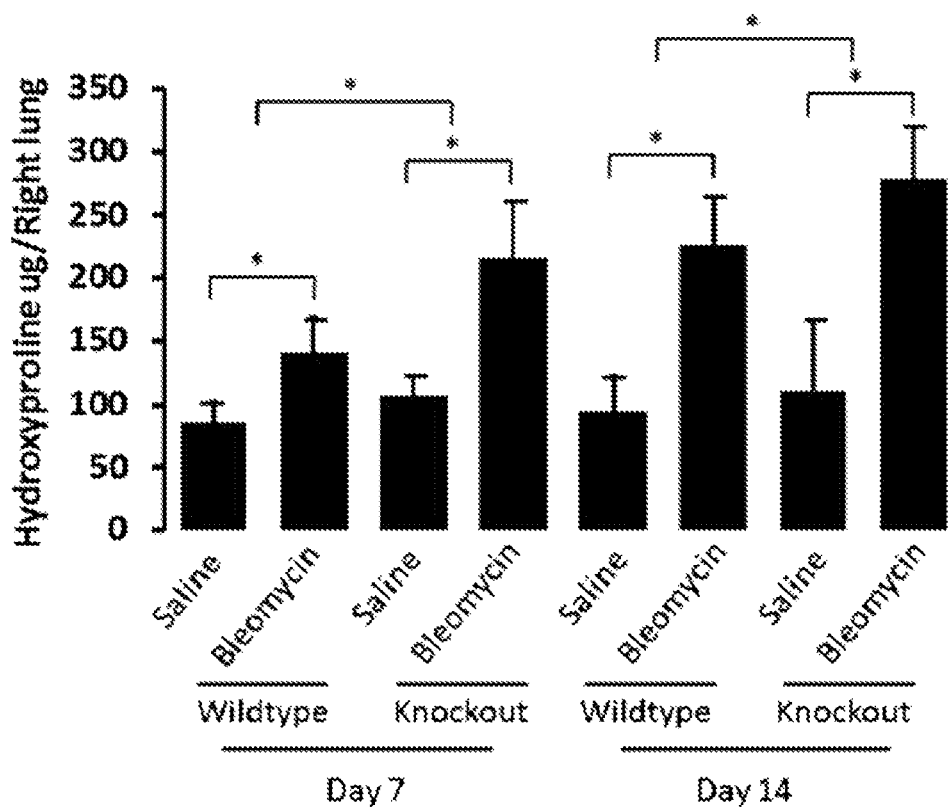
FIGS. 2A-2E illustrate the finding that DIO2-deficient (DIO2 KO) mice develops more severe fibrosis in bleomycin induction model. Mice at 8 weeks were administrated intratracheally with bleomycin at dose of 1.5 U/Kg, and sacrificed at day 7 and day 14.
Figure 2C:
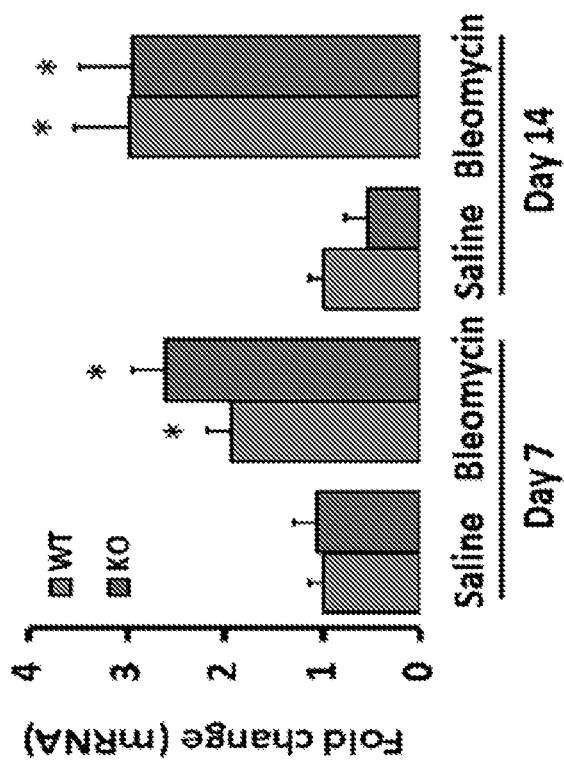
Figure 2B:
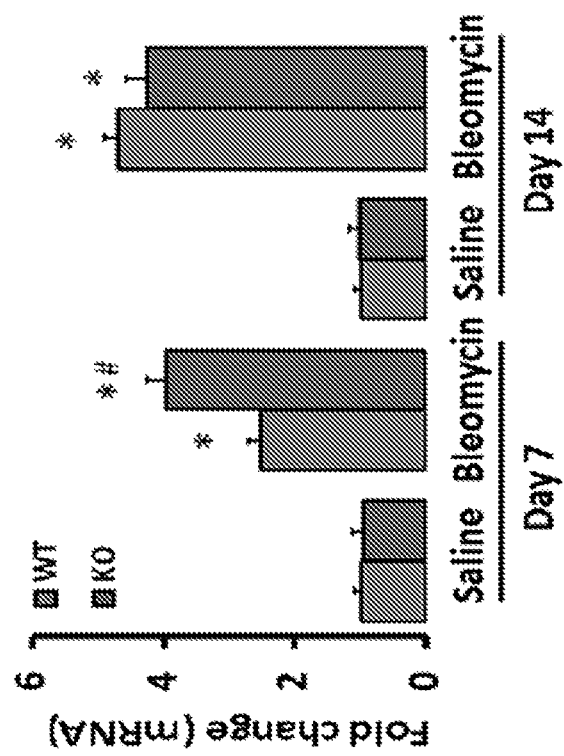

Mice lacking DIO2 developed more severe fibrosis following bleomycin intratracheal administration compared to controls, as assessed by dramatic increase in hydroxyproline content (FIG. 2A) and collagen expression, as evidenced by mRNA (FIG. 2B) and protein levels (FIG. 2C).

Figure 2D:
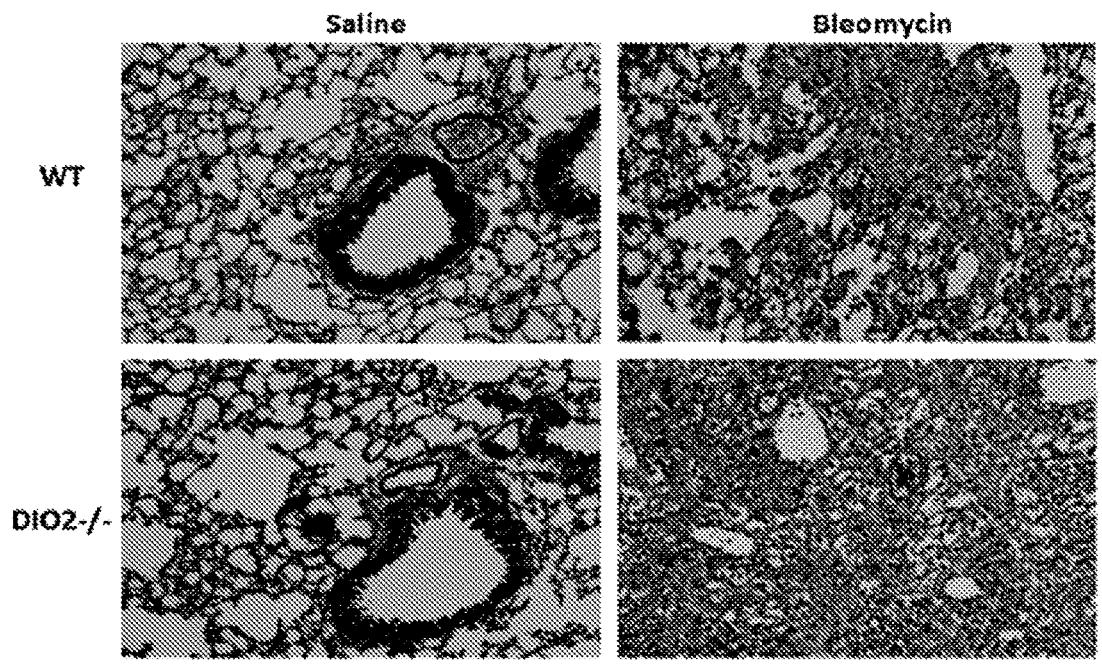
Figure 2E:
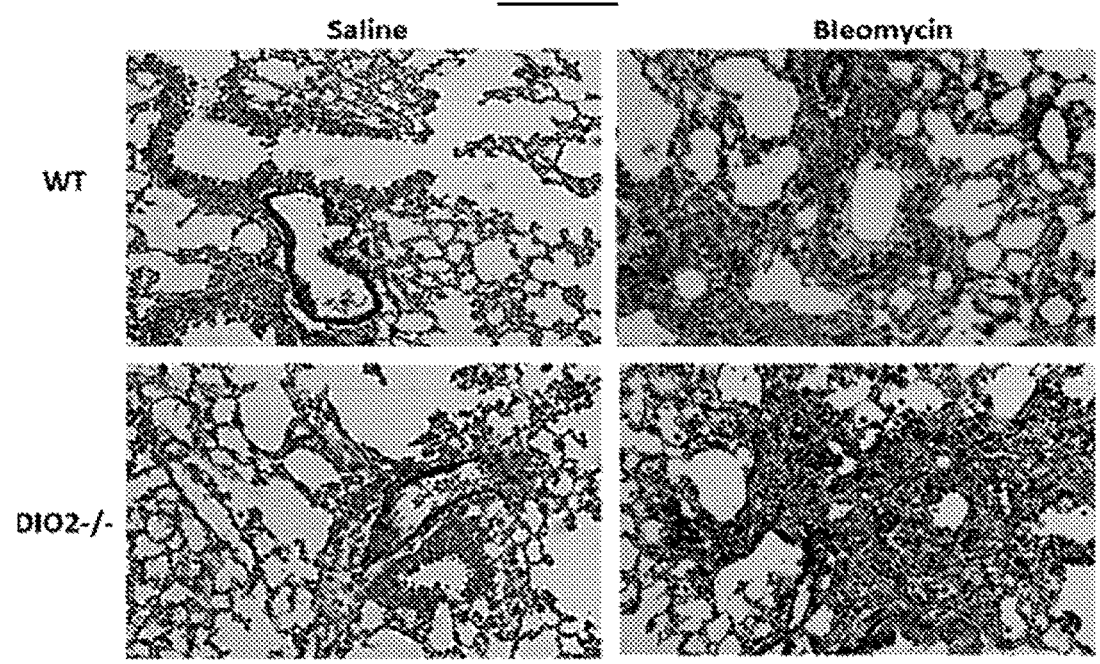

Histological and immunohistochemistry analysis using Masson's trichrome and a-smooth muscle actin demonstrated significantly increased collagen deposition (FIG. 2D) and myofibroblast differentiation (FIG. 2E) within lung interstitium in DIO2 knockout mice, as compared to wild type ones 14 days following bleomycin treatment, further corroborating earlier findings.

Figure 3A:
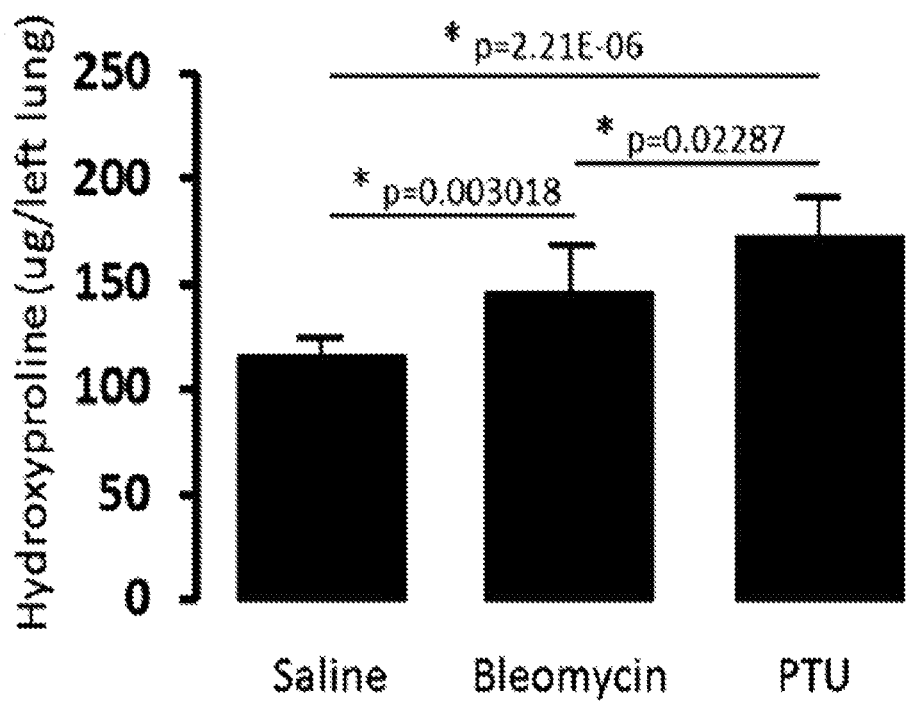
FIGS. 3A-3C illustrate the finding that PTU aggravates fibrosis in bleomycin-induced fibrosis in mice. Mice at 8 weeks were administrated intratracheally with bleomycin at dose of 1.5 U/Kg, 100 mg/kg of PTU was delivered intraperitoneally at day 3 and day 7, and sacrificed at day 14.
Figure 3B:
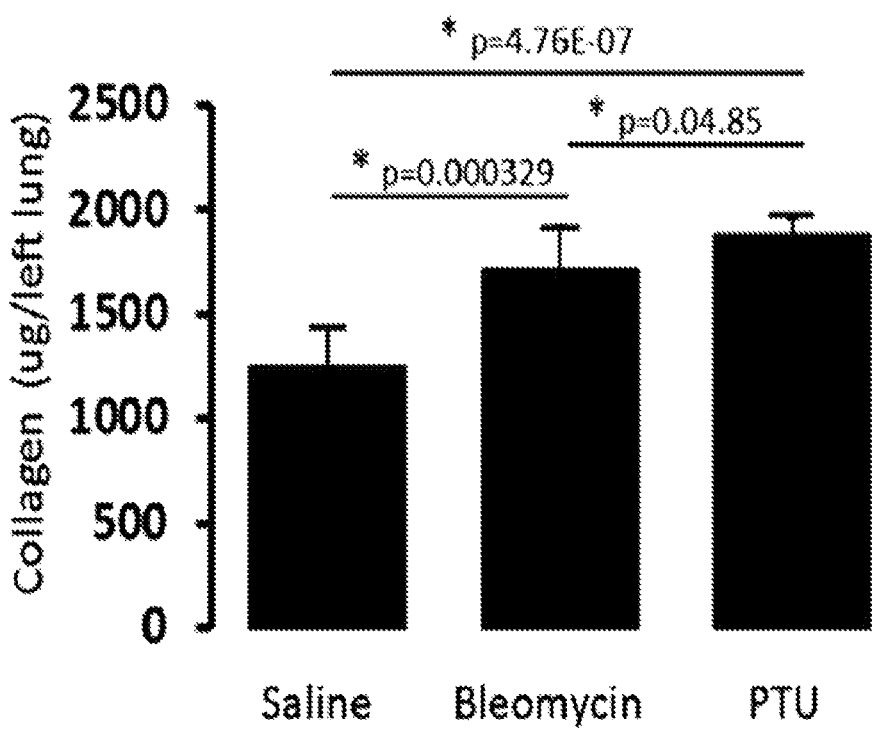
Figure 3C:
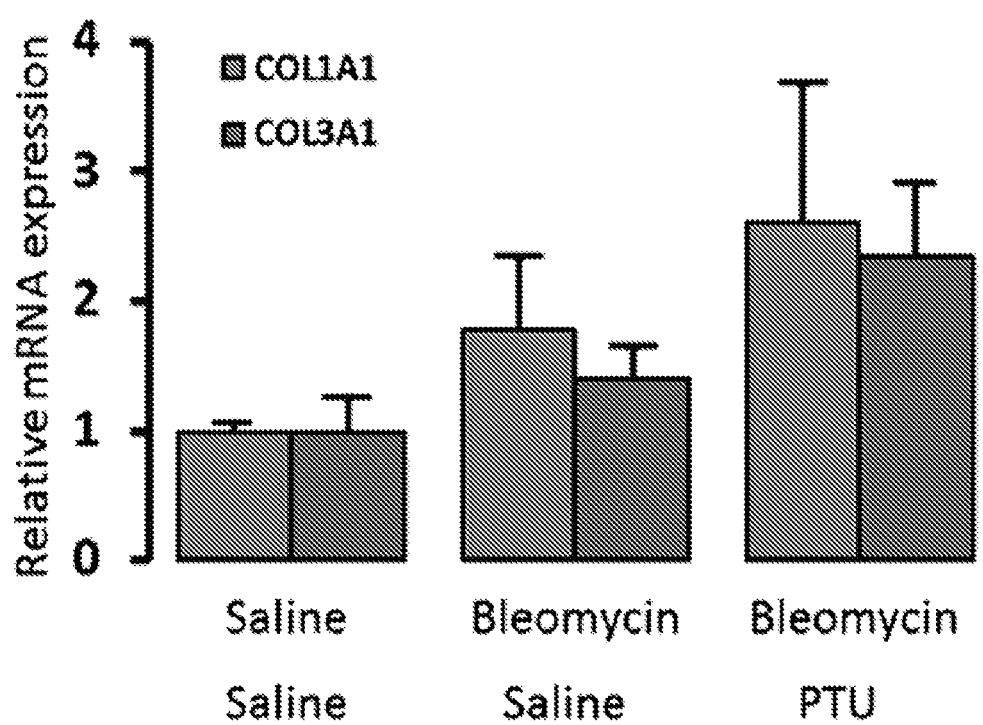
Figure 4A:
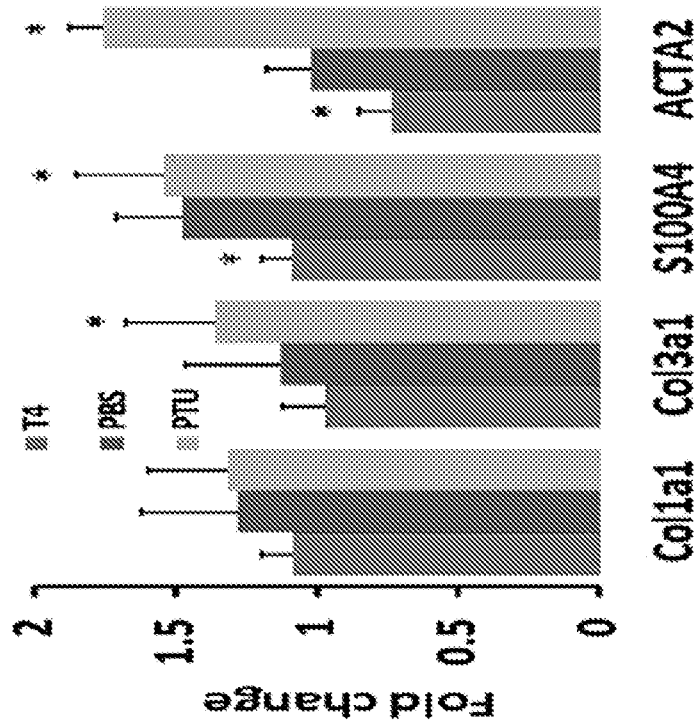
FIGS. 4A-4G illustrate the finding that intraperitoneal delivery of T4 after bleomycin instillation attenuates the pulmonary fibrosis. 40 mg/kg of T4 was intratracheally delivered 3 or 7 days after bleomycin treatment, mice were sacrificed at day 14.
Figure 4B:
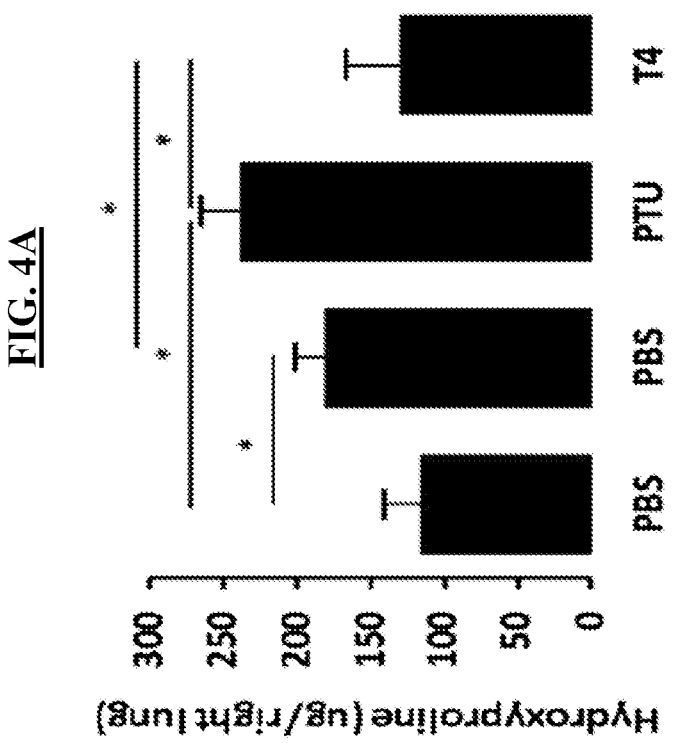
Figure 4C:
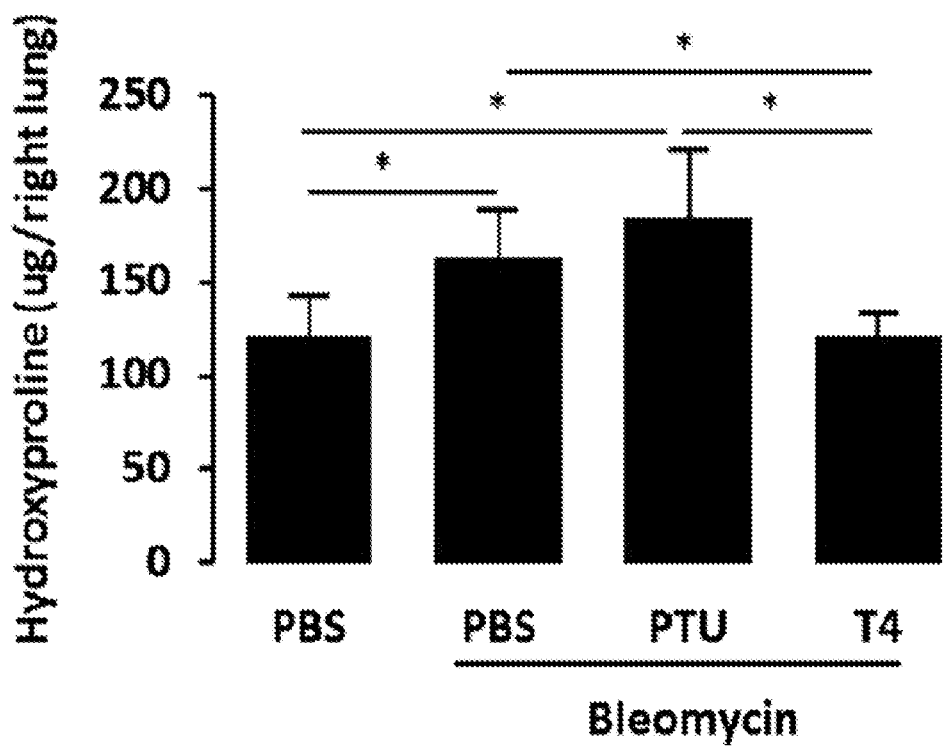
Figure 4D:
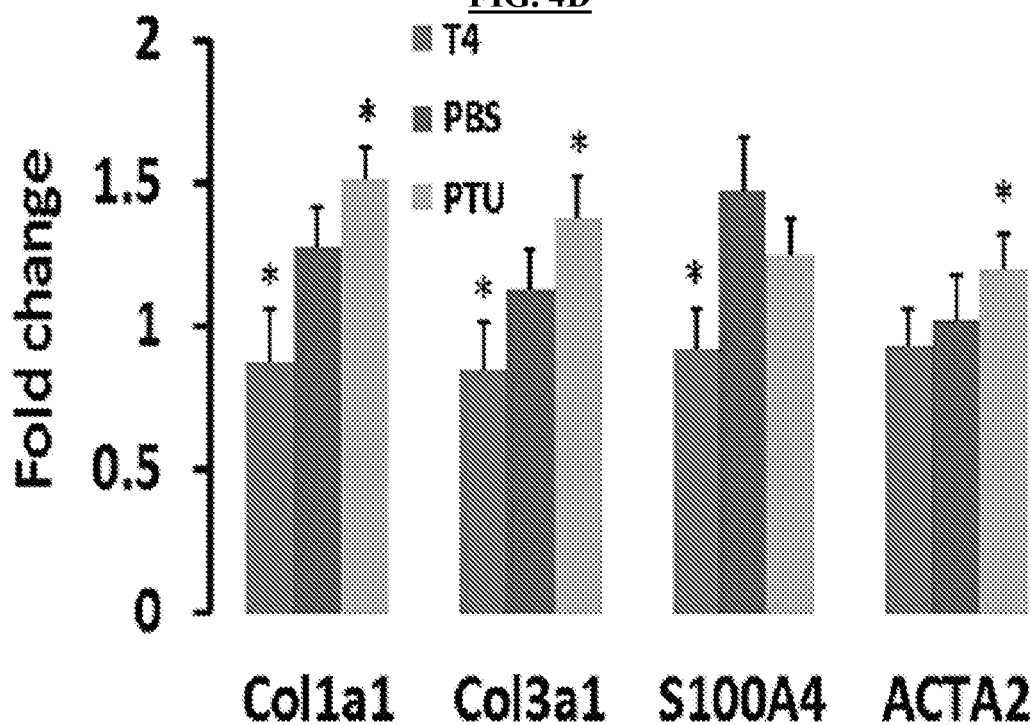
Figure 4E:
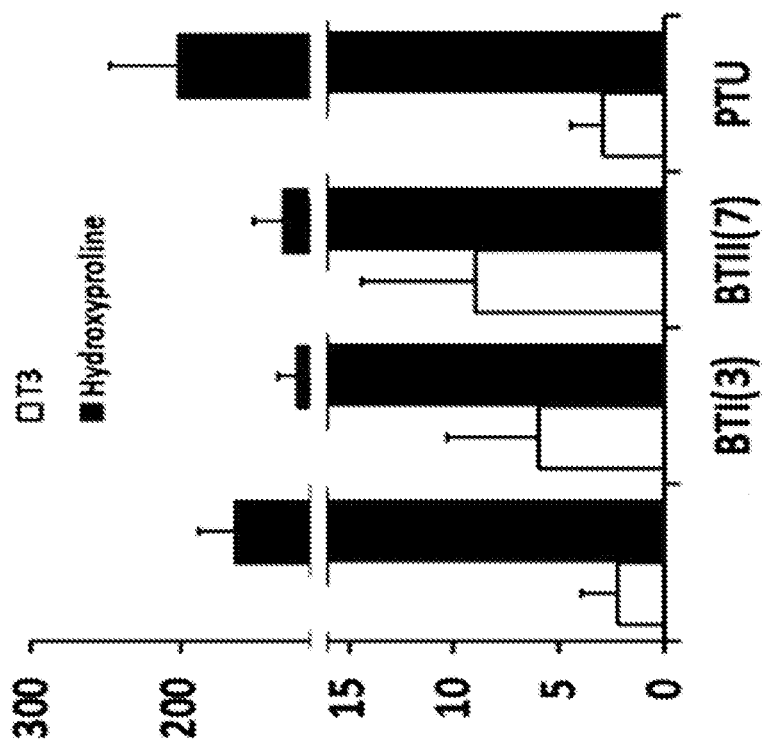
Figure 4F:
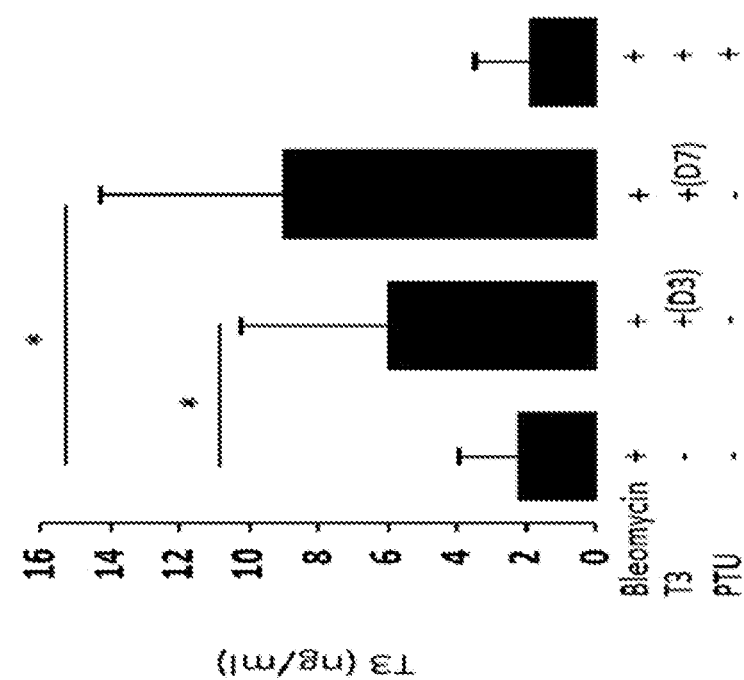
Figure 4G:
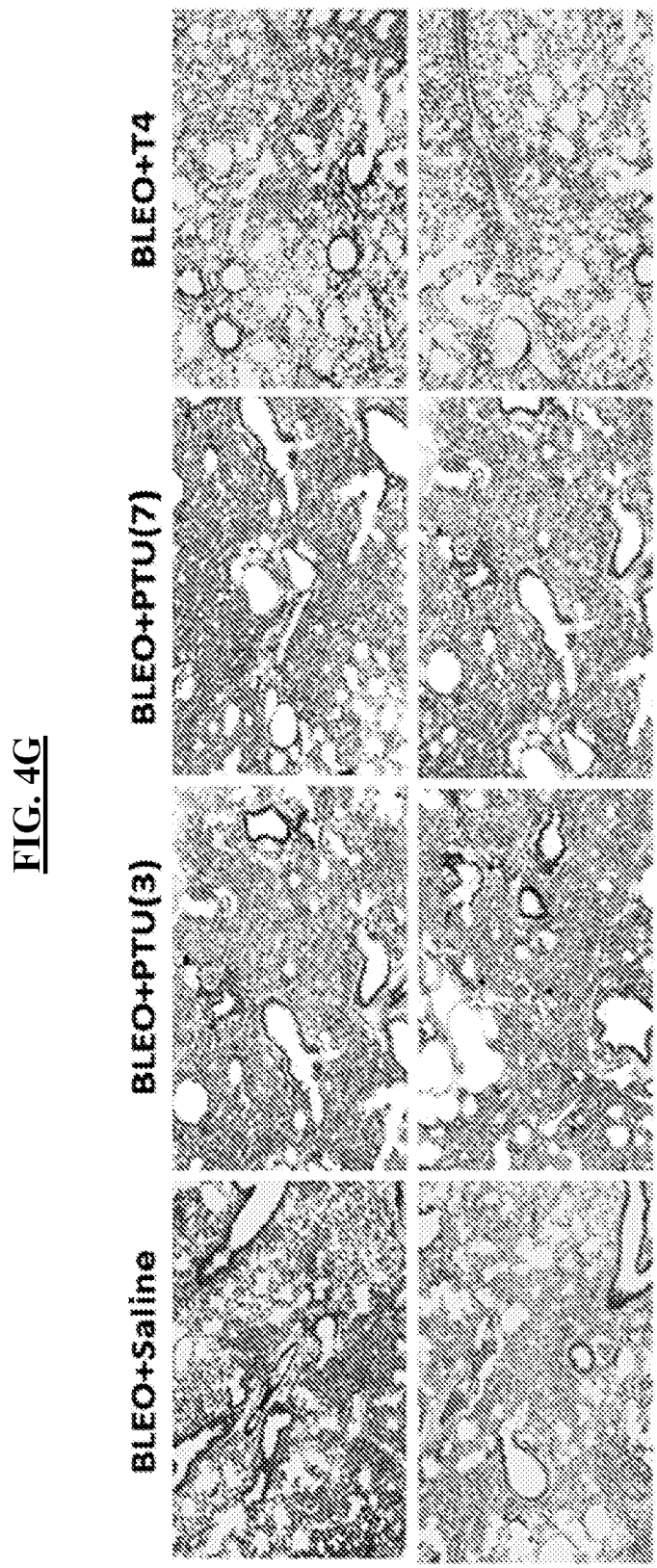

Similar results were obtained using propylthiouracil (PTU), a drug commonly used to treat hyperthyroidism. PTU inhibits iodine and peroxidase from their normal interactions with thyroglobulin to form T4 and T3. It also interferes with the conversion of T4 to T3. Since T3 is more potent than T4, this also reduces the activity of thyroid hormones. Administration of PTU through the intraperitoneal route led again to more severe bleomycin-induced lung fibrosis as estimated by significant elevation of hydroxyproline and collagen content within injured lung (FIGS. 3A-3C).

Example 3: T4 Treatment of Bleomycin-Induced Lung Fibrosis

Intraperitoneal delivery of T4 in mice at dose of 50 mg/kg following bleomycin exposure led to a significant attenuation of the fibrotic process, as assessed both by reduction in fibrotic markers and structural changes within the fibrotic lung (FIGS. 4A-4G). However, there was no statistically significant reduction on the hydroxyproline content 3 or 7 days after T4 administration, while an increase in circulating T3 levels following T4 treatment was observed, implying potential increase in thyroid hormone.

Figure 5B:
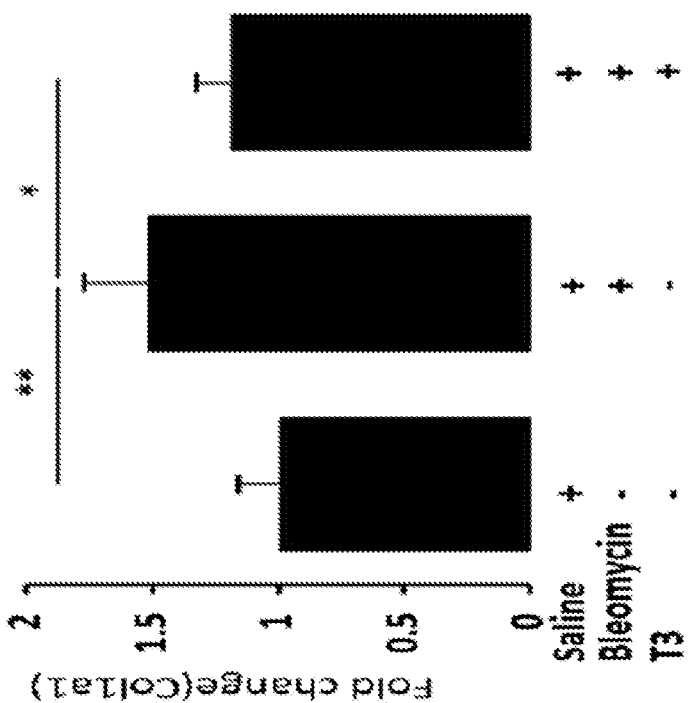
Figure 5A:
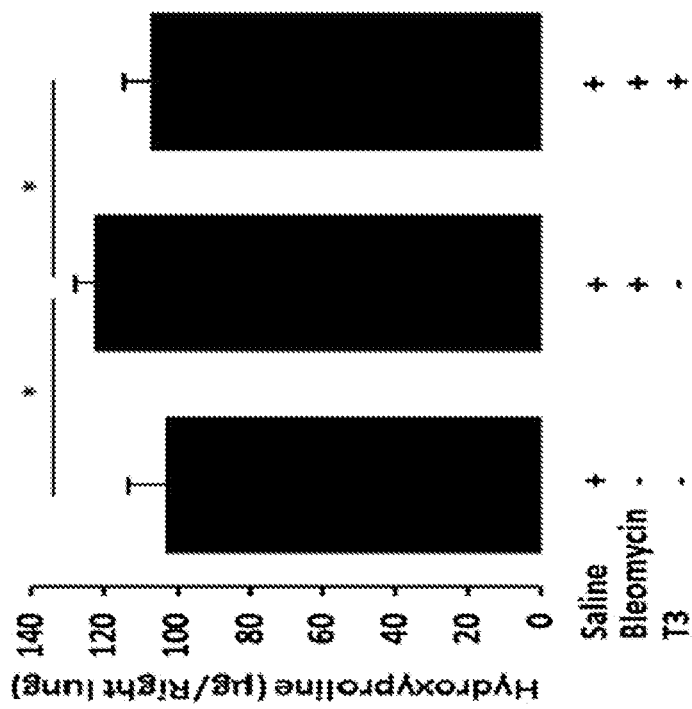
Figure 5C:
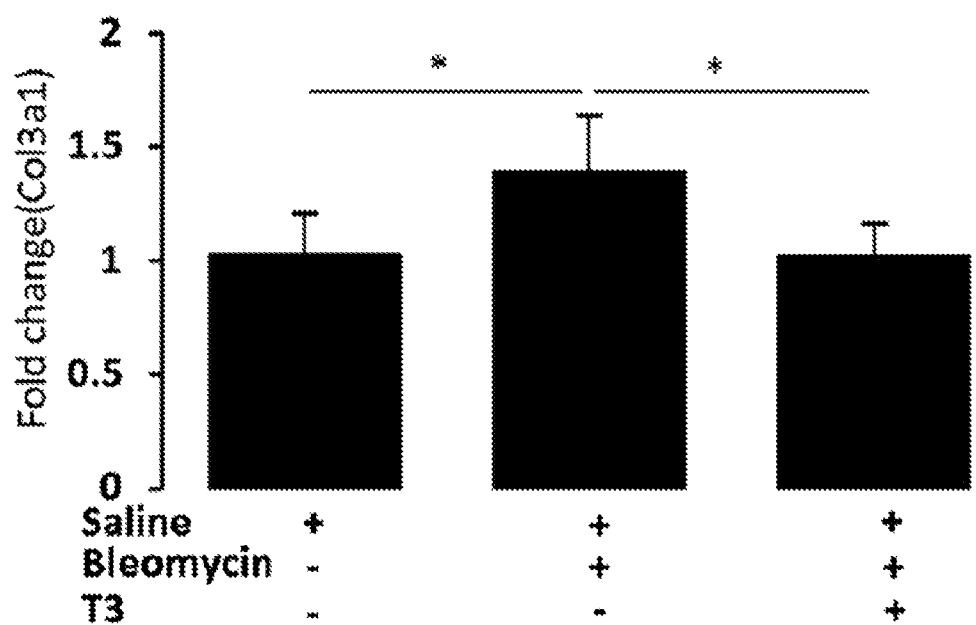
Figure 5D:
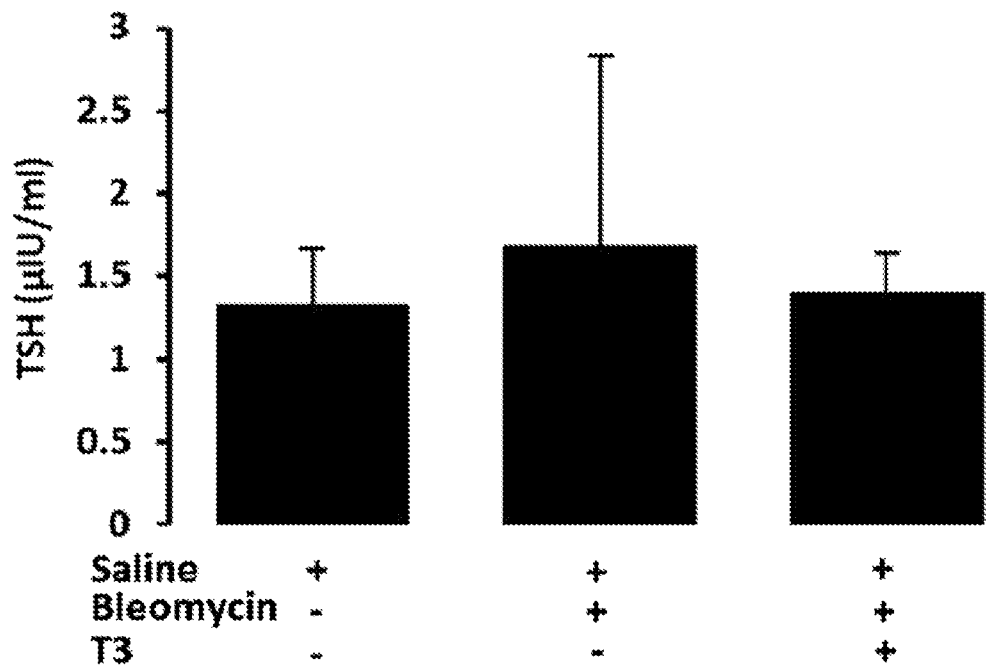

Example 4: Targeted Delivery of Thyroid Hormone (T3) in Bleomycin-Treated Animals Via Aerosolized Route In contrast to the systemic delivery, targeted administration of T3 at dose of 40 µg/kg via aerosolized route led to a statistically significant blunting of bleomycin-induced increases of hydroxyproline, without alterations in the T3 serum levels (FIGS. 5A-5C). Kaplan-Meier survival analysis demonstrated significant increase in survival in treated mice, highlighting a potential therapeutic effect.

Example 5

Experiments were run to delineate a potential mechanistic pathway through which thyroid hormones exert their protective role in the development and progression of experimental lung fibrosis. Gene expression analysis in alveolar epithelial cells isolated from bleomycin injured lungs before and after T3 aerosolized delivery revealed upregulation of several anti-apoptotic genes, as well as genes involved in stress response and increased cellular metabolism. Similar experiments were run in A549 lung adenocarcinoma cell lines before and after thyroid hormone administration.

"Rescue experiments" to determine whether T3 or T4 rescue the lung phenotype of DIO2 knockouts are performed. In these experiments, T3 or T4 is introduced to the lungs of Dio2 knockout mice before and after bleomycin-induced fibrosis.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating a fibrotic lung disease in a subject in need thereof, the method comprising administering to the subject a therapeutically effective amount of at least one thyroid hormone selected from the group consisting of T3 hormone and T4 hormone using an administration route selected from the group consisting of nasal, inhalational, intratracheal, intrapulmonary, intrabronchial, and inhalation.

2. The method of claim 1, wherein the lung tissue of the subject has upregulated DIO2 levels as compared to a subject who is not afflicted with the disease, and wherein the thyroid hormone comprises T4 hormone.

3. The method of claim 2, wherein the lung tissue of the subject has DIO2 levels that are at least about 50% higher than those in a subject not afflicted by the disease.

4. The method of claim 2, wherein the lung tissue of the subject has DIO2 levels that are at least about 100% higher than those in a subject not afflicted by the disease.

5. The method of claim 2, wherein the DIO2 levels are upregulated in terms of at least one selected from the group consisting of gene expression, mRNA expression and protein expression.

6. The method of claim 1, wherein the fibrotic lung disease comprises idiopathic pulmonary fibrosis.

7. The method of claim 6, wherein the lung tissue of the subject has upregulated DIO2 levels as compared to a subject who is not afflicted with the disease, and wherein the thyroid hormone comprises T4 hormone.

8. The method of claim 1, wherein the subject is further administered at least one additional agent that treats or reduces the symptoms of the fibrotic lung disease.

9. The method of claim 8, wherein the at least one additional agent comprises at least one selected from the group consisting of pirfenidone and nintadanib.

10. The method of claim 1, wherein the thyroid hormone is administered to the subject at a frequency selected from the group consisting of about three times a day, about twice a day, about once a day, about every other day, about every third day, about every fourth day, about every fifth day, about every sixth day and about once a week.

11. The method of claim 1, wherein the thyroid hormone is formulated as a dry powder blend.

12. The method of claim 11, wherein the dry powder blend comprising levothyroxine sodium hydrate.

13. The method of claim 12, wherein the dry powder blend further comprises lactose particles, comprising lactose.$H_2O$, gelatine and starch maize; sodium starch glycolate; magnesium stearate; and talc silicified, comprising talc purified and colloidal silicon dioxide.

14. The method of claim 1, wherein the subject is a mammal.

15. The method of claim 14, wherein the mammal is a human.

\* \* \* \* \*